United States Patent [19]
Rise

[11] Patent Number: 5,853,424
[45] Date of Patent: Dec. 29, 1998

[54] METHOD OF AND APPARATUS FOR PREVENTING TISSUE INGROWTH IN INFUSION CATHETERS

[75] Inventor: Mark T. Rise, Monticello, Minn.

[73] Assignee: Medtronic, Inc, Minneapolis, Minn.

[21] Appl. No.: 615,124

[22] Filed: Mar. 13, 1996

[51] Int. Cl.$^6$ .................................................. A61N 1/04
[52] U.S. Cl. ........................................ 607/117; 607/121
[58] Field of Search ................................... 607/117, 120, 607/121; 604/49, 51, 264, 265, 266

[56] References Cited

U.S. PATENT DOCUMENTS

| | | |
|---|---|---|
| 4,633,889 | 1/1987 | Talalla et al. . |
| 4,774,967 | 10/1988 | Zanakis et al. . |
| 4,961,954 | 10/1990 | Goldberg et al. ........................ 604/96 |
| 5,119,832 | 6/1992 | Xavier . |
| 5,423,877 | 6/1995 | Mackay ................................ 607/117 |
| 5,445,608 | 8/1995 | Chen et al. ............................. 604/20 |
| 5,458,631 | 10/1995 | Xavier ................................... 607/117 |

OTHER PUBLICATIONS

Geller, et al., "An Improved Constant Current Source for Micro–Iontophoretic Drug Application Studies", *Electroencephalography & Clinical Neurophysiology*, 1972, 33:430–432.

Hurlbert, R. John, et al., "Dose–response study of the pathological effects of chronically applied direct current stimulation on the normal rat spinal cord", *J. Neurosurg.*, vol. 79, Dec., 1993:905–916.

Jaffe, Lionel F., et al., "Neurites Grow Faster towards the Cathode than the Anode in a Steady Field", *J. Exp. Zool.*, (1979)209: 115–128.

Patgel, Nilesh, et al., "Orientation of Neurite Growth by Extracellular Electric Fields", *The Journal of Neuroscience*, vol. 2, No. 4 pp. 483–496, Apr. 1982.

*Primary Examiner*—Scott Getzow
*Attorney, Agent, or Firm*—Curtis D. Kinghorn; Harold R. Patton

[57] ABSTRACT

A weak, positive electric charge is induced at the distal or discharge end of an infusion catheter to inhibit tissue ingrowth relative to the discharge opening. The charge may be induced by connecting an electrode carried at the distal end to a suitable source of electric potential. Alternatively, a positively charged member or coating may be provided at the distal end of the catheter.

45 Claims, 3 Drawing Sheets

METHOD OF AND APPARATUS FOR PREVENTING TISSUE INGROWTH IN INFUSION CATHETERS

BACKGROUND OF THE INVENTION

1. Field of the Invention

This invention relates to fluid infusion catheters, and more particularly, to a method of and apparatus for preventing the ingrowth of tissue in infusion catheters by applying a particular electric charge or field to the catheter.

2. Description of the Related Art

Infusion catheters have long been employed to deliver fluids to local areas of internal organs. They are also used for intraspinal drug delivery. In each such application, the proximal end of the catheter is placed in fluid communication with a suitable source of medicament, and its distal end is positioned immediately adjacent to the organ or tissue intended to receive the medicament.

A problem typically encountered with infusion catheters, however, is the ingrowth of tissue into the distal end of the catheter, a problem exacerbated when tissue-growth medicaments are infused.

SUMMARY OF THE INVENTION

The method and apparatus for preventing tissue ingrowth according to the invention overcomes the problems of the prior art by utilizing an electric charge on the open, distal end of the catheter to prevent tissue ingrowth into the open end of the catheter.

More particularly, the invention is directed to an infusion catheter which has opposite proximal and distal ends in fluid communication with each other, the proximal end being adapted to be connected to a source of fluid, the distal end being adapted to be positioned adjacent to body tissue for delivery of fluid thereto. In accordance with the invention in its broader aspects, the catheter is provided with an electric element adapted to carry an electric charge and disposed in a position to influence the growth of the adjacent body tissue in and around the distal end.

In one form of the invention, the electric element comprises a charged coating carried by at least a portion of surface of the distal end and preferably comprising a primary amine functional coating, or a quaternary amine functional coating, or a cationic hydrogel coating.

The electric element may comprise a member affixed to the catheter in a position to be adjacent to the body tissue and having the charged coating on at least a portion of its surface. Such a member is suitably disposed at the distal end of the catheter.

Alternatively, the electric element may comprise an electrode carried by the catheter in a position to be adjacent to the body tissue and adapted to be electrically connected to a source of electric potential such as a battery or a capacitor.

The electric element may also comprise a pair of electrodes, one of them being disposed at the distal end in a position to be adjacent to the body tissue, the other being disposed between the first electrode and the proximal end. For purposes explained hereinbelow, a positive charge is induced at the first electrode and a negative charge at the other electrode.

The invention also provides a method of controlling natural tissue growth surrounding an infusion catheter which comprises the steps of providing a source of infusate; providing a catheter of the type described, infusing fluid from the source of infusate to the body tissue by way of a discharge aperture of the catheter; and providing an electrically polarized surface adjacent to the discharge aperture to influence the natural growth of body tissue in and around the distal end of the catheter.

These and other objects, features, and advantages of the invention will be apparent from the ensuing description in conjunction with the accompanying drawings.

DETAILED DESCRIPTION OF THE PREFERRED EMBODIMENTS

Figure 1:
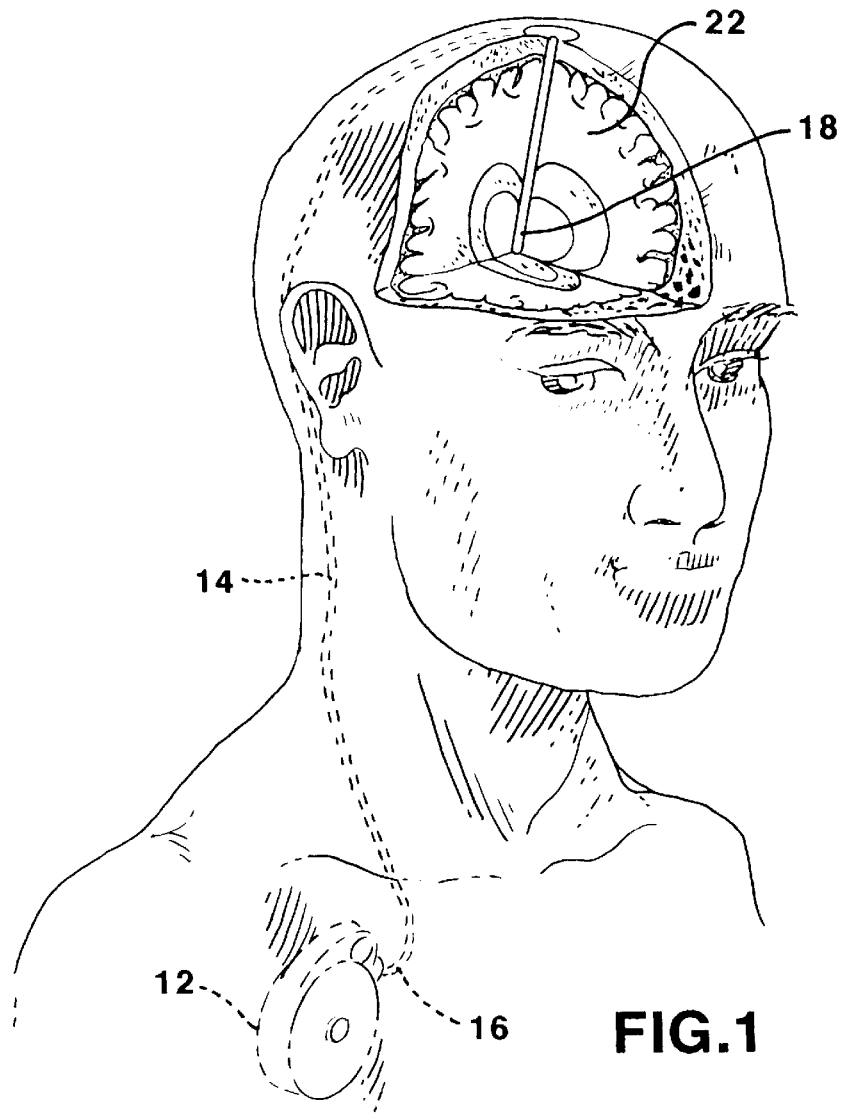
FIG. 1 is a schematic representation of an infusion-catheter fluid-delivery system surgically implanted in a patient.
Figure 2:
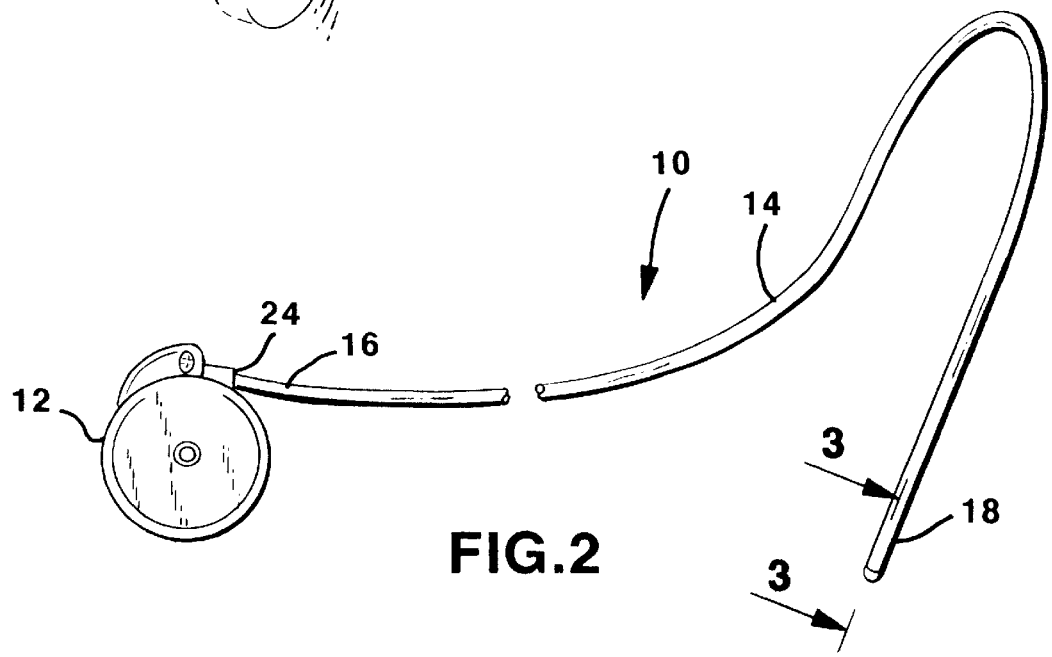
FIG. 2 is a plan view of an infusion-catheter fluid-delivery system of the type represented in FIG. 1, but removed from the patient, and including an infusion catheter according to the invention.
Figure 3:
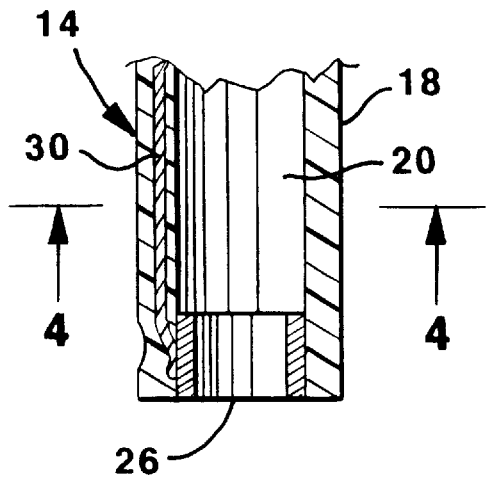
FIG. 3 is a greatly enlarged, partial, longitudinal sectional view of the infusion catheter of FIG. 2, taken along line 3 3 thereof.
Figure 4:
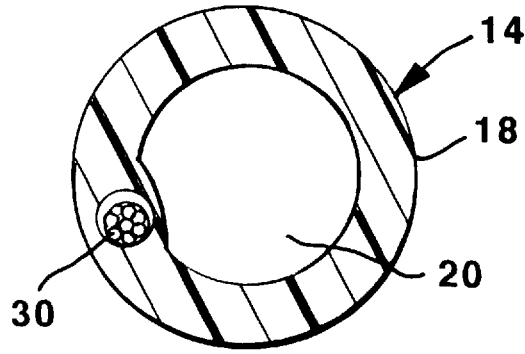
FIG. 4 is a further enlarged, cross-sectional view of the infusion catheter of FIGS. 2 and 3, taken along line 4 4 of FIG. 3.

Referring now to the drawings, and to FIGS. 1 to 4 in particular, an infusion-catheter fluid-delivery system 10 for medicaments comprises a combined fluid pump and reservoir 12 and an infusion catheter 14. A proximal end 16 of the infusion catheter is secured to pump-reservoir 12, whereas an opposite distal end 18 is adapted to be positioned immediately adjacent to the tissue intended to receive medicament. A lumen 20 extends from the proximal end to the distal end to conduct the flow of fluid therebetween.

Pump-reservoir 12 comprises any suitable means for conveying medicament from a suitable source through catheter 14. Fluid pump-reservoir 12 is preferably implanted in the patient and includes a self-contained reservoir for storing medicament, a pump (not shown) for drawing the medicament fluid from the reservoir and advancing it by way of infusion catheter 14 to the tissue to be treated, and a suitable power source, such as a battery capacitor, for energizing the pump. An example of a suitable pump-reservoir is the SynchroMed™ programmable pump, available from Medtronic, Inc. of Minneapolis, Minn. The pump-reservoir is surgically implanted in the patient and programmed to deliver prescribed amounts of medicament continuously, on demand, or at regularly scheduled intervals. Although it is preferred that the pump-reservoir be implanted in the patient, an external source of fluid may also be employed without departing from the scope of the invention.

Proximal end 16 of the catheter is secured to an outlet port 24 of pump-reservoir 12. In the example shown in FIG. 1, pump-reservoir 12 is surgically implanted in subcutaneous tissue, and infusion catheter 14 extends internally to the parenchyma of the patient's brain 22 so that medicament is conducted directly from the pump-reservoir to the brain tissue. This type of medicament delivery system is ideal for medications which are not readily or efficiently absorbed and delivered where needed by way of the digestive and circulatory systems. For example, nerve-growth factor cannot at present be directed to brain tissue effectively except by direct application using a catheter.

As noted hereinabove, a problem inherent in the direct delivery of medicaments to affected tissue is the ingrowth of tissue into the open distal end of the catheter, and this problem is enhanced when growth factors are infused. The present invention overcomes this problem by providing for application of a weak electric charge to distal end 18 of catheter 14, whereby ingrowth of tissue into the open end of the catheter is inhibited. More particularly, in the embodiment shown in FIGS. 1 to 4, distal end 18 of catheter 14 is provided with an electrode 26, which is electrically connected by means of a main electrical conductor 30 to a source of electric charge, such as battery 28 (FIG. 5) of pump-reservoir 12. Creating a positively charged electric field adjacent to distal end 18 of infusion catheter 14 will have the effect of inhibiting tissue growth into the open end of the catheter. Main conductor 30 is suitably an electrically conductive wire or filament integrally molded within the wall of catheter 14 so that it will be effectively insulated from fluids inside and outside of the catheter. Electrode 26 may be located on the inner surface of lumen 20 at the distal end 18 of infusion catheter 14.

Figure 5:
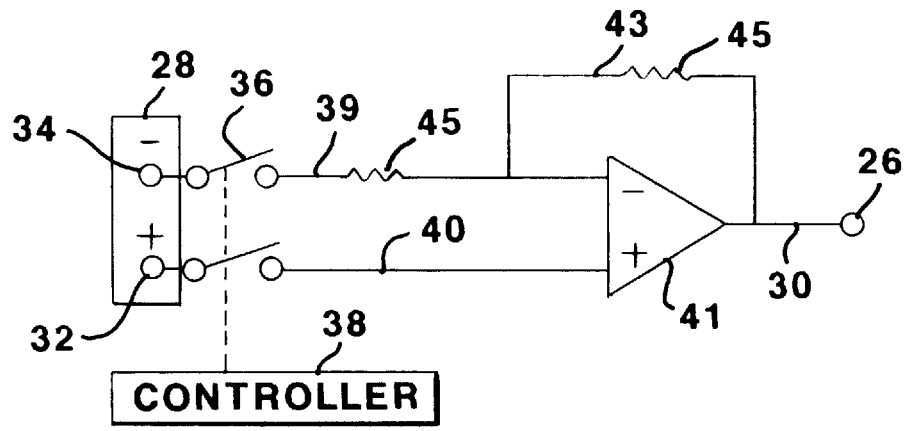
FIG. 5 is a schematic diagram of an electric circuit for an infusion-catheter fluid-delivery system.

FIG. 5 is an electrical diagram of the preferred circuitry for effecting an electric charge at distal end 18 of the catheter. Broadly stated, electrode 26 is interconnected to battery 28 of the pump. More particularly, the positive and negative terminals 32 and 34, respectively, of the battery are connected to a conventional switch 36, the relative position of the switch being established by a controller 38 of the pump. Primary electrical conductors 39, 40 of conventional form extend from switch 36 to an operative amplifier 41. Main conductor 30 extends from the outlet terminal of amplifier 41 to electrode 26. A bypass electrical conductor 43 extends between primary conductor 39 and main conductor 30. Resistances 45, each representing electrical resistance of a suitable predetermined magnitude, are incorporated in primary conductor 39 and bypass conductor 43, respectively, in order to establish, when switch 36 is closed, a substantially constant positive charge at the outlet terminal of operative amplifier 41 and thus at electrode 26. Preferably, the circuit is designed to provide an electric field at the electrode in the range of 0.5 to 1.5 volts/cm. Fields in this range have been found to establish the desired growth patterns in human nerve tissue.

Controller 38 may be programmed to open and close switch 36 intermittently, thereby establishing a positive charge at electrode 26 intermittently. Alternatively, the switch may be eliminated or remain closed to establish a constant electric potential at electrode 26. However, inclusion of a switch as represented at 36 in association with a controller as represented at 38 provides significant flexibility in the timing, duration, and frequency of an electric charge at electrode 26.

The system may be modified by selectively interconnecting electrode 26 to negative terminal 34 of the battery. This may readily be accomplished by reversing the connection of primary conductors 39, 40 to operative amplifier 41. When a negative charge is induced at the electrode, certain tissue cells will be drawn to grow in the direction of the negative charge. Under some circumstances, it might be desirable to stimulate growth toward distal end 18 of catheter 14. Once again, switch 36 may be employed to control the timing, duration, and polarity of the charged electric field applied at the distal end of the catheter.

Figure 6:
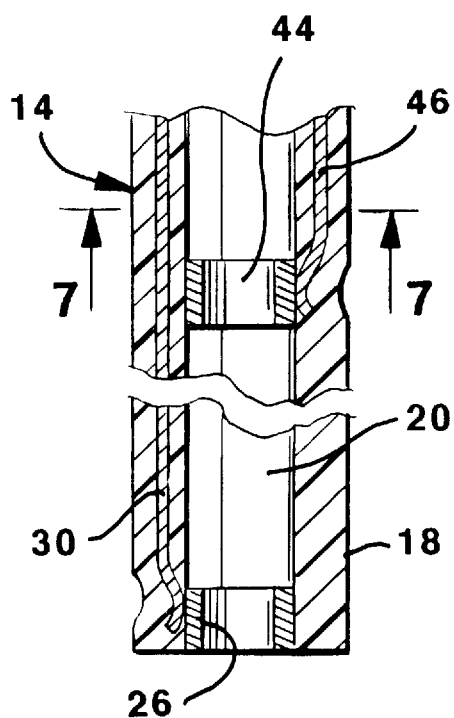
FIG. 6 is a view similar to that of FIG. 3, but of a modified embodiment of the infusion catheter according to the invention.
Figure 7:
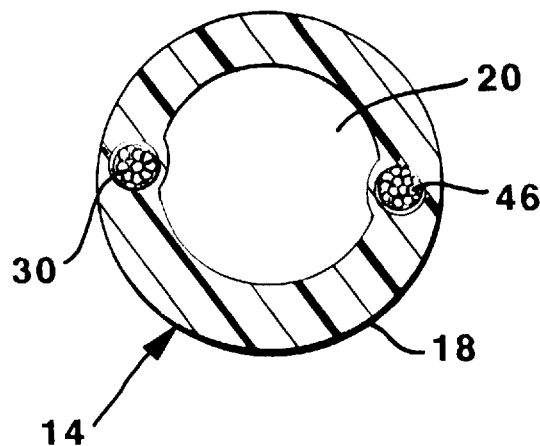
FIG. 7 is an enlarged, cross-sectional view of the infusion catheter of FIG. 6, taken along line 7 7 thereof.

Referring now to FIGS. 6 and 7, the system may be modified by providing a second electrode 44 upstream from distal end 18 of the catheter. Electrode 44 may be located on the inner surface of lumen 20. In one embodiment, electrode 44 may be located on the inner surface of lumen 20 proximal to electrode 26. This electrode 44 is electrically connected to a suitable source of electric potential such as pump battery terminals 32, 34 by means of an electrical conductor 46 which, preferably, is integrally molded within the side wall of infusion catheter 14. Second electrode 44 may be used to withdraw certain medicaments back into the catheter from distal end 18. For example, certain growth factors are attracted to a negative electric field. Therefore, during static growth-factor delivery periods, a weak negative charge may be induced at second electrode 44 thereby drawing any growth factor adjacent to the distal end of the catheter back upstream within the infusion catheter. By thus urging the growth factor in the reverse direction within the catheter, say at the conclusion of the infusion cycle, the influence of the growth factor inside the catheter may be minimized until the next infusion cycle.

Figure 8:
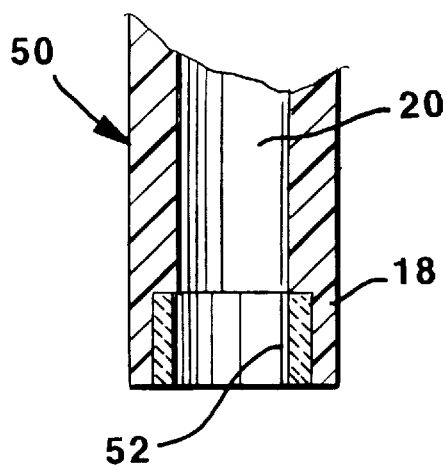
FIG. 8 is a view similar to that of FIG. 3 or FIG. 6, but of a third embodiment of the infusion catheter according to the invention.

A third embodiment of the infusion catheter according to the invention is shown in FIG. 8. In this embodiment, a charged member 52 is inserted in a suitable aperture provided in distal end 18 of a catheter 50. Charged member 52 presents a polymer surface treated by a conventional process to induce a positive or, in some cases, negative charge thereon. For example, a positively charged surface may be established by an ethylene/ammonia plasma surface treatment. This treatment results in the deposition of primary amine functional groups $NH_2$ on the surface, which exhibit a positive charge.

Alternatively, a quaternary amine functional coating may be applied to the surface. With this type of coating, the hydrophobic portion of the molecule preferentially attaches to the polymer surface, and the positively charged portion faces outwardly from the polymer surface, thereby exhibiting a positive charge on the surface.

Still another method of establishing a positive charge on the surface of charged member 52 comprises application of a cationic hydrogel coating, which is covalently bonded to the surface by a ceric ion grafting process. Examples of suitable monomers for this purpose include aminopropyl methacrylamide (APMA) and methacrylamidopropyltrinethyl ammonium chloride (MAPTAC).

Regardless of the process used, a charged member 52 exhibiting the desired positive or negative charge is provided in catheter 50 immediately adjacent to distal tip 18 or spaced along the length of the catheter depending on the particular application contemplated for the fluid delivery system in which the catheter is employed.

Figure 9:
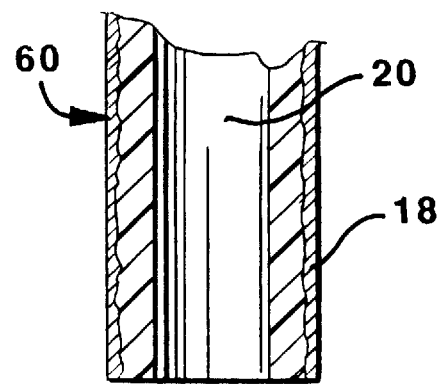
FIG. 9 is a view similar to that of FIG. 3, FIG. 6, or FIG. 8, but of a fourth embodiment of the infusion catheter according to the invention.

A fourth embodiment of the invention is shown in FIG. 9. Here, the surface of distal end 18 of an infusion catheter 60 is coated with a positively or negatively charged material by one or more of the coating processes described hereinabove, the coating being carried out directly on the surface of the catheter to establish a charged environment along a predetermined length thereof Establishment of an electric charge along the length of, at the distal end of, or at a location spaced from the distal end of an infusion catheter may be useful for either or both of two purposes: to controlling the ingrowth of tissue into the distal, open end of the catheter, and to direct and withdraw the flow of certain medicaments which are attracted or repelled by weak electric fields. The electric charge may be supplied from an internal source of electric potential such as an implanted battery or capacitor or, alternatively by an external source of conventional form. This system provides added control and predictability over the precise flow and directed delivery of medicaments to affected tissue.

The infusion process and operation of the pump may be regulated by a controller which may be externally located or incorporated in fluid pump-reservoir 12. The previously discussed SynchroMed™ system includes an internal, programmable controller for regulating the medicament infusion process. This known controller may be readily adapted for use in accordance with the invention.

While the invention has been particularly described in connection with certain specific embodiments thereof, this is by way of illustration and not of limitation, and the scope of the appended claims should be construed as broadly as the prior art will permit.

What is claimed is:

1. An infusion catheter for providing fluid to body tissue when the catheter is inserted into body tissue, the catheter having opposite proximal and distal ends in fluid communication with each other, the proximal end being connectable to a source of fluid, the distal end being positionable adjacent to body tissue for delivery of fluid thereto, and an electric element carrying a static electric charge and disposed in a position to influence the growth of body tissue in and around the distal end when the distal end of the catheter is placed in body tissue, wherein the electric element comprises a charged coating carried by at least a portion of a surface of the distal end.

2. The catheter of claim 1, wherein the electric element comprises a charged coating carried by at least a portion of a surface of the distal end.

3. The catheter of claim 2, wherein the charged coating is selected from the group comprising primary amine functional coatings, quaternary amine functional coatings, and cationic hydrogel coatings.

4. The catheter of claim 2, wherein the charged coating is affixed to the catheter in a position to be adjacent to the body tissue when the distal end of the catheter is positioned next to the body tissue.

5. The catheter of claim 4, wherein the charged coating is selected from the group comprising primary amine functional coatings, quaternary amine functional coatings, and cationic hydrogel coatings.

6. The catheter of claim 4, wherein the coated member is disposed at the distal end of the catheter.

7. The catheter of claim 1, wherein the electric element further comprises a first electrode carried by the catheter in a position to be adjacent to the body tissue and adapted to be electrically connected to a source of electric potential.

8. The catheter of claim 7, further comprising a battery electrically connected to the first electrode carried by the catheter.

9. The catheter of claim 8, further comprising an operative amplifier electrically connected between the battery and the first electrode to induce an electric charge at the first electrode.

10. The catheter of claim 9, further comprising a switch electrically connected between the first electrode and the battery to selectively open and close the electric circuit between the battery and the first electrode.

11. The catheter of claim 10, further comprising a controller for opening and closing the switch.

12. The catheter of claim 7, further comprising a capacitor for storing and providing electric charge electrically connected to the first electrode.

13. The catheter of claim 1, wherein the electric element comprises a first and a second electrode carried by the catheter and adapted to be electrically connected to a source of electric potential, the first electrode being disposed at the distal end in a position to be adjacent to the body tissue, the second electrode being disposed intermediate the first electrode and the proximal end.

14. The catheter of claim 13, including means for inducing a positive charge at the first or second electrode and a negative charge at the second or first electrode, respectively.

15. A catheter for infusion of fluid into body tissue comprising:
   a catheter body having a proximal and a distal end;
   a lumen extending between the proximal end and the distal end and adapted at the proximal end to be placed in fluid communication with a source of infusate;
   the distal end formed with a fluid discharge aperture fluidly connected to the lumen;
   the proximal end spaced from the distal end;
   an electric element provided adjacent to the discharge aperture, the electric element having a static electric charge whereby the electric charge is presented to tissue surrounding the element when the catheter is placed in body tissue, whereby the direction of tissue growth relative to the fluid discharge aperture is influenced in accordance with the polarity of the electric charge.

16. An infusion-catheter fluid-delivery system for delivering medicaments to tissue comprising:
   a combined fluid pump and reservoir having an outlet port;
   an infusion catheter having a proximal end secured to the pump-reservoir and an opposite distal end adapted to be positioned immediately adjacent to the tissue intended to receive medicament, the catheter having a lumen extending from the proximal end to the distal end of the catheter to conduct flow of fluid therebetween, the proximal end of the catheter being secured to the outlet port of the pump-reservoir;
   an electrode located on the distal end of the catheter, the electrode being electrically connected by means of a main electrical conductor to a source of electric charge, the electrode having a static electric charge.

17. A system to prevent the ingrowth of tissue in infusion catheters comprising:
   an infusion catheter having opposite proximal and distal ends in fluid communication with each other, the proximal end being adapted to be connected to a source of fluid, the distal end being adapted to be positioned adjacent to body tissue for delivery of fluid thereto, and an electric element carrying a static electric charge and disposed in a position to influence the growth of the adjacent body tissue in and around the distal end, wherein the electric element comprises a charged coating carried by at least a portion of a surface of the distal end, wherein the charged coating is selected from the group comprising primary amine functional coatings, quaternary amine functional coatings, and cationic hydrogel coatings, the charged coating being affixed to the catheter in a position to be adjacent to the body tissue;

a battery electrically interconnected to the electric element by an electric circuit.

18. The catheter of claim 17, wherein the electric circuit comprises an operative amplifier electrically connected between the battery and the electrode to induce a positive charge at the electrode.

19. The catheter of claim 18, including a switch electrically connected in the electric circuit between the battery and the electrode to selectively open and close the circuit between the battery and the electrode.

20. The catheter of claim 19, including a controller for opening and closing the switch.

21. The catheter of claim 17, wherein the electric element comprises a first and a second electrode carried by the catheter and adapted to be electrically connected to a source of electric potential, the first electrode being disposed at the distal end in a position to be adjacent to the body tissue, the second electrode being disposed intermediate the first electrode and the proximal end.

22. The catheter of claim 21, including means for inducing a positive charge at the first or second electrode and a negative charge at the second or first electrode, respectively.

23. A system to prevent the ingrowth of tissue in infusion catheters comprising:
   an infusion catheter having opposite proximal and distal ends in fluid communication with each other, the proximal end being adapted to be connected to a source of fluid, the distal end being adapted to be positioned adjacent to body tissue for delivery of fluid thereto, and an electric element adapted to carry a static electric charge and disposed in a position to influence the growth of the adjacent body tissue in and around the distal end, wherein the electric element comprises a charged coating carried by at least a portion of a surface of the distal end, wherein the charged coating is selected from the group comprising primary amine functional coatings, quaternary amine functional coatings, and cationic hydrogel coatings, the charged coating being affixed to the catheter in a position to be adjacent to the body tissue, wherein the electric element comprises a first and a second electrode carried by the catheter and adapted to be electrically connected to a source of electric potential, the first electrode being disposed at the distal end in a position to be adjacent to the body tissue, the second electrode being disposed intermediate the first electrode and the proximal end;
   a battery electrically interconnected to the electric element by an electric circuit, wherein the electric circuit comprises an operative amplifier electrically connected between the battery and the first and second electrodes to induce an electric charge at the first electrode, the electric circuit including a switch connected in the electric circuit to selectively open and close the circuit between the battery and the first and second electrodes, the electric circuit also including a controller for opening and closing the switch; and
   means for inducing a positive charge at the first or second electrode and a negative charge at the second or first electrode, respectively.

24. A system to prevent the ingrowth of tissue in infusion catheters comprising:
   an infusion catheter having opposite proximal and distal ends in fluid communication with each other, the proximal end being adapted to be connected to a source of fluid, the distal end being adapted to be positioned adjacent to body tissue for delivery of fluid thereto, and an electric element adapted to carry a static electric charge and disposed in a position to influence the growth of the adjacent body tissue in and around the distal end, wherein the electric element comprises an electrode carried by the catheter in a position to be adjacent to the body tissue and adapted to be electrically connected to a source of electric potential;
   a battery electrically interconnected to the electric element by an electric circuit.

25. The catheter of claim 24, wherein the electric circuit comprises an operative amplifier electrically connected between the battery and the electrode to induce a positive charge at the electrode.

26. The catheter of claim 25, including a switch electrically connected in the electric circuit to selectively open and close the circuit between the battery and the electrode.

27. The catheter of claim 26, including a controller for opening and closing the switch.

28. The catheter of claim 24, wherein the electric element comprises a first and a second electrode carried by the catheter and adapted to be electrically connected to a source of electric potential, the first electrode being disposed at the distal end in a position to be adjacent to the body tissue, the second electrode being disposed intermediate the first electrode and the proximal end.

29. The catheter of claim 28, including means for inducing a positive charge at the first or second electrode and a negative charge at the second or first electrode, respectively.

30. A system to prevent the ingrowth of tissue in infusion catheters comprising:
   an infusion catheter having opposite proximal and distal ends in fluid communication with each other, the proximal end being adapted to be connected to a source of fluid, the distal end being adapted to be positioned adjacent to body tissue for delivery of fluid thereto, and an electric element adapted to carry a static electric charge and disposed in a position to influence the growth of the adjacent body tissue in and around the distal end, wherein the electric element comprises an electrode carried by the catheter in a position to be adjacent to the body tissue and adapted to be electrically connected to a source of electric potential, wherein the electric element comprises a a first and a second electrode carried by the catheter and adapted to be electrically connected to a source of electric potential, the first electrode being disposed at the distal end in a position to be adjacent to the body tissue, the second electrode being disposed intermediate the first electrode and the proximal end;
   a battery electrically interconnected to the electric element by an electric circuit, wherein the electric circuit comprises an operative amplifier electrically connected between the battery and the electrode to induce a positive charge at the first or the second electrode and a negative charge at the second or the first electrode, respectively, the electric circuit including a switch electrically connected in the electric circuit to selectively open and close the circuit between the battery and the first and the second electrode, the electric circuit also including a controller for opening and closing the switch; and
   means for inducing a positive charge at the first or the second electrode and a negative charge at the second or the first electrode, respectively.

31. A method of controlling natural tissue growth surrounding an infusion catheter comprising the steps of:
   providing a source of infusate;

providing a catheter having a proximal end in fluid communication with the source of infusate, a distal end adapted to be positioned adjacent to the body tissue in an operative position, and a discharge aperture formed at the distal end;

infusing fluid from the source of infusate to the body tissue by way of the discharge aperture;

providing static electrically polarized surface adjacent to the discharge aperture to influence the natural growth of body tissue in and around the distal end of the catheter.

32. A method of controlling natural tissue growth surrounding an infusion catheter comprising the steps of:

providing a source of infusate;

providing a catheter having a proximal end in fluid communication with the source of infusate, a distal end adapted to be positioned adjacent to the body tissue in an operative position, and a discharge aperture formed at the distal end;

infusing fluid from the source of infusate to the body tissue by way of the discharge aperture;

providing a static electric field to the discharge aperture to influence the natural growth of body tissue in and around the distal end of the catheter.

33. A method of controlling natural tissue growth surrounding an infusion catheter comprising the steps of:

providing a source of infusate;

providing a catheter having a lumen and having a proximal end in fluid communication with the source of infusate, a distal end adapted to be positioned adjacent to the body tissue in an operative position, and a discharge aperture formed at the distal end;

infusing fluid from the source of infusate to the body tissue by way of the discharge aperture;

providing an electrically polarized surface within the lumen adjacent to the discharge aperture to influence the natural growth of body tissue in and around the distal end of the catheter.

34. An infusion catheter for providing fluid to body tissue when the catheter is inserted into body tissue, the catheter having a lumen with an inner lumen surface, the catheter having opposite proximal and distal ends in fluid communication with each other through the lumen, the proximal end being connectable to a source of fluid, the distal end being positionable adjacent to body tissue for delivery of fluid thereto, and an electric element carrying an electric charge, the electric element located on the inner surface of the lumen to influence the growth of body tissue in and around the distal end when the distal end of the catheter is placed in body tissue.

35. The catheter of claim 34 wherein the electric element comprises a first electrode electrically connected to a source of electric potential.

36. The catheter of claim 35 further comprising a battery electrically connected to the first electrode.

37. The catheter of claim 36 further comprising an operative amplifier electrically connected between the battery and the first electrode to induce an electric charge at the first electrode.

38. The catheter of claim 37 further comprising a switch electrically connected between the first electrode and the battery to selectively open and close the electric circuit between the battery and the first electrode.

39. The catheter of claim 38 further comprising a controller for opening and closing the switch.

40. The catheter of claim 35 further comprising a capacitor for storing and providing electric charge, the capacitor being electrically connected to the first electrode.

41. The catheter of claim 40 further comprising an operative amplifier connected between the capacitor and the first electrode to induce an electric charge at the first electrode.

42. The catheter of claim 41 further comprising a switch electrically between the first electrode and the capacitor to selectively open and close the electric circuit between the capacitor and the first electrode.

43. The catheter of claim 42 further comprising a controller for opening and closing the switch.

44. The catheter of claim 35 further comprising a second electrode carried by the catheter within the lumen between the first electrode and the proximal end and adapted to be electrically connected to a source of electric potential.

45. The catheter of claim 44 including means for inducing a positive charge at the first or second electrode and a negative charge at second or first electrode, respectively.

* * * * *